United States Patent
Truckai et al.

(10) Patent No.: US 9,597,118 B2
(45) Date of Patent: Mar. 21, 2017

(54) BONE ANCHOR APPARATUS AND METHOD

(75) Inventors: Csaba Truckai, Saratoga, CA (US); John H. Shadduck, Tiburon, CA (US)

(73) Assignee: DFine, Inc., South Jordan, UT (US)

( * ) Notice: Subject to any disclaimer, the term of this patent is extended or adjusted under 35 U.S.C. 154(b) by 456 days.

(21) Appl. No.: 12/683,358

(22) Filed: Jan. 6, 2010

(65) Prior Publication Data

US 2010/0174320 A1 Jul. 8, 2010

Related U.S. Application Data

(60) Provisional application No. 61/204,507, filed on Jan. 7, 2009.

(51) Int. Cl.
*A61B 17/04* (2006.01)
*A61B 17/70* (2006.01)
*A61B 17/86* (2006.01)

(52) U.S. Cl.
CPC .......... *A61B 17/70* (2013.01); *A61B 17/7001* (2013.01); *A61B 17/8685* (2013.01)

(58) Field of Classification Search
CPC ............ A61B 17/7032; A61B 17/7035; A61B 17/7037; A61B 17/7011; A61B 17/7002
USPC .......................... 606/300–321, 329, 246–278
See application file for complete search history.

(56) References Cited

U.S. PATENT DOCUMENTS

| | | |
|---|---|---|
| 3,349,840 A | 10/1967 | Tope et al. |
| 4,250,887 A | 2/1981 | Dardik et al. |
| 4,265,618 A | 5/1981 | Herskovitz et al. |
| 4,280,233 A | 7/1981 | Raab |
| 4,294,251 A | 10/1981 | Grennwald et al. |
| 4,338,925 A | 7/1982 | Miller |
| 4,377,168 A | 3/1983 | Rzasa et al. |
| 4,386,603 A | 6/1983 | Mayfield |
| 4,433,677 A | 2/1984 | Ulrich et al. |
| 4,573,454 A | 3/1986 | Hoffman |
| 4,611,582 A | 9/1986 | Duff |
| 4,653,489 A | 3/1987 | Tronzo |
| 4,735,625 A | 4/1988 | Davidson |

(Continued)

FOREIGN PATENT DOCUMENTS

| | | |
|---|---|---|
| WO | WO 02/064062 | 8/2002 |
| WO | WO 02/087416 | 11/2002 |

(Continued)

OTHER PUBLICATIONS

B. Heublein, R. Rohde, V. Kaese, M. Niemeyer, W. Hartung, A. Haverich, "Biocorrosion of magnesium alloys: a new principle in cardiovascular implant technology?", Heart, 2003; 89:651-656.

(Continued)

*Primary Examiner* — Matthew Lawson
(74) *Attorney, Agent, or Firm* — Stoel Rives LLP

(57) ABSTRACT

A bone anchor can include an elongated body and a plurality of separate elements. The bone anchor can be configured to be insertable into bone. The bone anchor can be coupleable to a spine treatment apparatus. The bone anchor can be revisable so that after a treatment interval attached to a spine treatment apparatus, the spine treatment apparatus can be detached and the bone anchor revised by removing the plurality of separate elements from the bone thus allowing a new anchor to be implanted in the bone.

14 Claims, 5 Drawing Sheets

(56) References Cited

U.S. PATENT DOCUMENTS

| | | |
|---|---|---|
| 4,772,287 A | 9/1988 | Ray et al. |
| 4,773,402 A | 9/1988 | Asher et al. |
| 4,849,223 A | 7/1989 | Pratt et al. |
| 4,959,104 A | 9/1990 | Iino et al. |
| 4,963,151 A | 10/1990 | Ducheyene et al. |
| 4,969,888 A | 11/1990 | Scholten et al. |
| 4,969,906 A | 11/1990 | Kronman |
| 5,030,220 A | 7/1991 | Howland |
| 5,037,437 A | 8/1991 | Matsen |
| 5,051,482 A | 9/1991 | Tepic |
| 5,108,404 A | 4/1992 | Scholten |
| 5,130,950 A | 7/1992 | Orban et al. |
| 5,145,250 A | 9/1992 | Planck et al. |
| 5,306,275 A * | 4/1994 | Bryan .................. 606/914 |
| 5,431,654 A | 7/1995 | Nic |
| 5,514,135 A | 5/1996 | Earle |
| 5,542,928 A | 8/1996 | Evans et al. |
| 5,574,075 A | 11/1996 | Draemert |
| 5,593,407 A | 1/1997 | Reis |
| 5,679,299 A | 10/1997 | Gilbert et al. |
| 5,693,099 A | 12/1997 | Harle |
| 5,788,711 A | 8/1998 | Lehner et al. |
| 5,810,815 A | 9/1998 | Morales |
| 5,814,681 A | 9/1998 | Hino et al. |
| 5,827,289 A | 10/1998 | Reiley et al. |
| 5,954,716 A | 9/1999 | Sharkey et al. |
| 5,972,015 A | 10/1999 | Scribner et al. |
| 6,019,760 A | 2/2000 | Metz-Stavenhagen et al. |
| 6,048,346 A | 4/2000 | Reiley et al. |
| 6,075,067 A | 6/2000 | Lidgren |
| 6,122,549 A | 9/2000 | Sharkey et al. |
| 6,171,312 B1 | 1/2001 | Beaty |
| 6,214,012 B1 * | 4/2001 | Karpman et al. ............. 606/93 |
| 6,231,615 B1 | 5/2001 | Preissman |
| 6,235,043 B1 | 5/2001 | Reiley et al. |
| 6,236,020 B1 | 5/2001 | Friedman |
| 6,241,734 B1 | 6/2001 | Scribner |
| 6,248,110 B1 | 6/2001 | Reiley et al. |
| 6,261,289 B1 | 7/2001 | Levy |
| 6,264,659 B1 | 7/2001 | Ross et al. |
| 6,280,456 B1 | 8/2001 | Scribner et al. |
| 6,309,420 B1 | 10/2001 | Preissman |
| 6,312,254 B1 | 11/2001 | Friedman |
| 6,316,885 B1 | 11/2001 | Collins et al. |
| 6,319,255 B1 | 11/2001 | Grundei et al. |
| 6,332,894 B1 | 12/2001 | Stalcup et al. |
| 6,358,254 B1 | 3/2002 | Anderson |
| 6,364,883 B1 | 4/2002 | Santilli |
| 6,375,659 B1 | 4/2002 | Erbe et al. |
| 6,395,007 B1 | 5/2002 | Bhatnagar et al. |
| 6,425,923 B1 | 7/2002 | Stalcup et al. |
| 6,436,143 B1 | 8/2002 | Ross et al. |
| 6,439,439 B1 | 8/2002 | Rickard |
| 6,440,169 B1 | 8/2002 | Elberg et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,485,436 B1 | 11/2002 | Truckai |
| 6,524,102 B2 | 2/2003 | Davis |
| 6,554,830 B1 | 4/2003 | Chappius |
| 6,558,428 B2 | 5/2003 | Park |
| 6,565,572 B2 * | 5/2003 | Chappius .................. 600/300 |
| 6,582,446 B1 | 6/2003 | Marchosky |
| 6,610,079 B1 | 8/2003 | Li et al. |
| 6,613,054 B2 | 9/2003 | Scribner et al. |
| 6,620,185 B1 | 9/2003 | Harvie et al. |
| 6,622,731 B2 | 9/2003 | Daniel et al. |
| 6,632,235 B2 | 10/2003 | Weikel et al. |
| 6,676,664 B1 | 1/2004 | Al-Assir |
| 6,683,280 B1 | 1/2004 | Wofford et al. |
| 6,706,069 B2 | 3/2004 | Berger |
| 6,709,149 B1 | 3/2004 | Tepic |
| 6,712,852 B1 | 3/2004 | Chung et al. |
| 6,719,773 B1 | 4/2004 | Boucher et al. |
| 6,723,095 B2 | 4/2004 | Hammerslag |
| 6,726,691 B2 | 4/2004 | Osorio et al. |
| 6,736,537 B2 | 5/2004 | Coffeen et al. |
| 6,740,093 B2 | 5/2004 | Hochschuler et al. |
| 6,753,358 B2 | 6/2004 | Fisher et al. |
| 6,767,936 B2 | 7/2004 | Walz et al. |
| 6,783,515 B1 | 8/2004 | Miller |
| 6,814,736 B2 | 11/2004 | Reiley et al. |
| 6,832,988 B2 | 12/2004 | Sproul |
| 6,872,403 B2 | 3/2005 | Pienkowski et al. |
| 6,899,713 B2 | 5/2005 | Shaolian et al. |
| 6,929,640 B1 | 8/2005 | Underwood |
| 6,964,667 B2 | 11/2005 | Shaolian et al. |
| 6,979,341 B2 | 12/2005 | Scribner et al. |
| 6,979,352 B2 | 12/2005 | Reynolds |
| 6,981,981 B2 | 1/2006 | Reiley et al. |
| 6,985,061 B2 | 1/2006 | Hafskjold et al. |
| 6,989,011 B2 | 1/2006 | Paul et al. |
| 7,008,433 B2 | 3/2006 | Voellmicke et al. |
| 7,029,472 B1 | 4/2006 | Fortin |
| 7,044,954 B2 | 5/2006 | Reiley et al. |
| 7,066,938 B2 | 6/2006 | Slivka et al. |
| 7,081,125 B2 | 7/2006 | Edwards et al. |
| 7,108,696 B2 | 9/2006 | Daniel et al. |
| 7,112,201 B2 | 9/2006 | Truckai et al. |
| 7,112,205 B2 | 9/2006 | Carrison |
| 7,115,163 B2 | 10/2006 | Zimmermann |
| 7,153,306 B2 | 12/2006 | Ralph et al. |
| 7,153,307 B2 | 12/2006 | Scribner et al. |
| 7,156,861 B2 | 1/2007 | Scribner et al. |
| 7,160,020 B2 | 1/2007 | Sand |
| 7,166,121 B2 | 1/2007 | Reiley et al. |
| 7,191,285 B2 | 3/2007 | Scales |
| 7,226,481 B2 | 6/2007 | Kuslich |
| 7,241,303 B2 | 7/2007 | Reiss et al. |
| 7,250,055 B1 * | 7/2007 | Vanderwalle .................. 606/92 |
| 7,252,672 B2 | 8/2007 | Yetkinler |
| 7,261,720 B2 | 8/2007 | Stevens et al. |
| 7,273,523 B2 | 9/2007 | Wenz |
| 7,335,200 B2 | 2/2008 | Carli |
| 7,335,203 B2 | 2/2008 | Winslow et al. |
| 7,431,763 B2 | 10/2008 | Zimmermann |
| 7,510,579 B2 | 3/2009 | Preissman |
| 7,559,932 B2 | 7/2009 | Truckai et al. |
| 7,662,133 B2 | 2/2010 | Scarborough et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,717,918 B2 | 5/2010 | Truckai et al. |
| 7,717,947 B1 * | 5/2010 | Wilberg et al. .............. 606/304 |
| 7,722,620 B2 | 5/2010 | Truckai et al. |
| 7,722,624 B2 | 5/2010 | Boucher et al. |
| 8,070,753 B2 | 12/2011 | Truckai et al. |
| 8,192,442 B2 | 6/2012 | Truckai et al. |
| 8,348,955 B2 | 1/2013 | Truckai et al. |
| 9,005,210 B2 | 4/2015 | Truckai et al. |
| 2002/0026195 A1 | 2/2002 | Layne et al. |
| 2002/0068974 A1 | 6/2002 | Kuslich et al. |
| 2002/0099385 A1 | 7/2002 | Ralph et al. |
| 2002/0147497 A1 | 10/2002 | Belef et al. |
| 2002/0156483 A1 | 10/2002 | Voellmicke et al. |
| 2002/0161373 A1 | 10/2002 | Osorio et al. |
| 2002/0165582 A1 | 11/2002 | Porter |
| 2003/0032929 A1 | 2/2003 | McGuckin |
| 2003/0083662 A1 | 5/2003 | Middleton |
| 2003/0130738 A1 | 7/2003 | Hovda et al. |
| 2003/0220648 A1 | 11/2003 | Osorio et al. |
| 2003/0233096 A1 | 12/2003 | Osorio et al. |
| 2004/0006347 A1 | 1/2004 | Sproul |
| 2004/0024410 A1 | 2/2004 | Olson |
| 2004/0083002 A1 | 4/2004 | Belef et al. |
| 2004/0110285 A1 | 6/2004 | Lendlein |
| 2004/0111088 A1 * | 6/2004 | Picetti ............... A61B 17/7001 606/265 |
| 2004/0138748 A1 | 7/2004 | Boyer, II et al. |
| 2004/0158247 A1 | 8/2004 | Sitiso et al. |
| 2004/0172132 A1 | 9/2004 | Ginn |
| 2004/0186576 A1 | 9/2004 | Biscup et al. |
| 2004/0193171 A1 | 9/2004 | DiMauro et al. |
| 2004/0228898 A1 | 11/2004 | Ross et al. |

(56) References Cited

U.S. PATENT DOCUMENTS

| | | |
|---|---|---|
| 2004/0267272 A1 | 12/2004 | Henniges |
| 2005/0010231 A1 | 1/2005 | Myers |
| 2005/0015148 A1 | 1/2005 | Jansen et al. |
| 2005/0055026 A1 | 3/2005 | Biderman et al. |
| 2005/0113843 A1 | 5/2005 | Arramon |
| 2005/0180806 A1 | 8/2005 | Green et al. |
| 2005/0209595 A1 | 9/2005 | Karmon |
| 2005/0222681 A1 | 10/2005 | Richley et al. |
| 2005/0245938 A1 | 11/2005 | Kochan |
| 2005/0251149 A1 | 11/2005 | Wenz |
| 2006/0052743 A1 | 3/2006 | Reynolds |
| 2006/0052794 A1 | 3/2006 | McGill et al. |
| 2006/0074433 A1 | 4/2006 | McGill et al. |
| 2006/0079905 A1 | 4/2006 | Beyar et al. |
| 2006/0084979 A1* | 4/2006 | Jackson ............... 606/61 |
| 2006/0095138 A1 | 5/2006 | Truckai et al. |
| 2006/0100635 A1 | 5/2006 | Reiley et al. |
| 2006/0122614 A1 | 6/2006 | Truckai et al. |
| 2006/0122624 A1 | 6/2006 | Truckai et al. |
| 2006/0150862 A1 | 7/2006 | Zhao et al. |
| 2006/0264967 A1 | 11/2006 | Ferreyro et al. |
| 2007/0027230 A1 | 2/2007 | Beyar et al. |
| 2007/0112299 A1 | 5/2007 | Smit et al. |
| 2007/0118144 A1 | 5/2007 | Truckai et al. |
| 2007/0162043 A1 | 7/2007 | Truckai et al. |
| 2007/0185231 A1 | 8/2007 | Liu et al. |
| 2007/0191858 A1 | 8/2007 | Truckai et al. |
| 2007/0191964 A1 | 8/2007 | Preissman |
| 2007/0233077 A1 | 10/2007 | Khalili |
| 2007/0233089 A1 | 10/2007 | DiPoto et al. |
| 2007/0233148 A1 | 10/2007 | Truckai et al. |
| 2007/0288014 A1 | 12/2007 | Shadduck et al. |
| 2007/0299445 A1 | 12/2007 | Shadduck et al. |
| 2007/0299450 A1 | 12/2007 | Her et al. |
| 2008/0021465 A1 | 1/2008 | Shadduck et al. |
| 2008/0021466 A1 | 1/2008 | Shadduck et al. |
| 2008/0058818 A1* | 3/2008 | Schwab ............ A61B 17/7032 606/328 |
| 2008/0103505 A1 | 5/2008 | Fransen |
| 2008/0132956 A1* | 6/2008 | Biedermann et al. ........ 606/300 |
| 2008/0195112 A1 | 8/2008 | Liu et al. |
| 2008/0208260 A1 | 8/2008 | Truckai et al. |
| 2009/0024161 A1 | 1/2009 | Bonutti et al. |
| 2010/0055646 A1* | 3/2010 | Zhao ............................ 433/174 |
| 2010/0145397 A1* | 6/2010 | Overes et al. ................ 606/319 |
| 2011/0022092 A1 | 1/2011 | Trieu |
| 2012/0303036 A1 | 11/2012 | Truckai |

FOREIGN PATENT DOCUMENTS

| | | | | |
|---|---|---|---|---|
| WO | WO 2004/075954 | | 9/2004 | |
| WO | WO 2006/031490 | | 3/2006 | |
| WO | WO 2006/062916 | | 6/2006 | |
| WO | WO 2006/062939 | | 6/2006 | |
| WO | WO 2006/130491 | | 12/2006 | |
| WO | WO 2007/028120 | | 3/2007 | |
| WO | WO 2008/125049 | * | 4/2008 | ............... A31C 8/00 |
| WO | WO 2008/097855 | | 8/2008 | |
| WO | WO 2009/108893 | | 9/2009 | |

OTHER PUBLICATIONS

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.

EPO Search Report re App. No. 11 00 7504, dated Oct. 18, 2011.

Exam Report for EPO App. 05 848 386.8 dated Feb. 6, 2013 in 4 pgs.

Exam Report for EPO App. 05 848 386.8 dated Sep. 18, 2009 in 5 pgs.

International Search Report, mailing date May 31, 2006, PCT/US2005/044055, 4 pg.

International Search Report, mailing date Jun. 20, 2006, PCT/US2005/043984, 2 pg.

Japanese Office Action, re Application No. JP 2007-544613, dated Mar. 29, 2011 in 8 pages, with complete English translation.

* cited by examiner

BONE ANCHOR APPARATUS AND METHOD

CROSS-REFERENCE TO RELATED APPLICATIONS

This application claims the benefit of U.S. Provisional Patent Application No. 61/204,507, filed Jan. 7, 2009, entitled BONE ANCHOR APPARATUS AND METHOD, the entire contents of which are hereby incorporated by reference herein and should be considered a part of this specification. This application is also related to U.S. patent application Ser. No. 11/780,967, filed Jul. 20, 2007, entitled SPINE TREATMENT DEVICES AND METHODS, the entire contents of which are hereby incorporated by reference herein and should be considered a part of this specification.

BACKGROUND OF THE INVENTION

Field of the Invention

This disclosure relates to medical instruments and more particularly to bone anchor systems for spine treatments, wherein the anchors can be configured for revision following a treatment interval.

Description of the Related Art

Thoracic and lumbar spinal disorders are a major socio-economic concern in the United States affecting over 70% of the population at some point in life. Low back pain is the most common musculoskeletal complaint requiring medical attention, and is the fifth most common reason for all physician visits. The annual prevalence of low back pain ranges from 15% to 45% and is the most common activity-limiting disorder in persons under the age of 45.

Degenerative changes in the intervertebral disc often play a role in the etiology of low back pain. Many surgical and non-surgical treatments exist for patients with degenerative disc disease (DDD), but often the outcome and efficacy of these treatments are uncertain. In current practice, when a patient has intractable back pain, the physician's first approach is conservative treatment with the use of pain killing pharmacological agents, bed rest and limitations on spinal segment motion. Only after an extended period of conservative treatment will the physician consider a surgical solution, which often is spinal fusion of the painful vertebral motion segment. Fusion procedures are highly invasive procedures that carry surgical risk as well as the risk of transition syndrome described below, wherein adjacent levels will be at increased risk for facet and discogenic pain.

More than 150,000 lumbar and nearly 200,000 cervical spinal fusions are performed each year to treat common spinal conditions such as degenerative disc disease and spondylolisthesis, or misaligned vertebrae. Some 28 percent are multi-level, meaning that two or three vertebrae are fused. Such fusions "weld" unstable vertebrae together to eliminate pain caused by their movement. While there have been significant advances in spinal fusion devices and surgical techniques, the procedure does not always work reliably. In one survey, the average clinical success rate for pain reduction was about 75%; and long time intervals were required for healing and recuperation (3-24 months, average 15 months). Probably the most significant drawback of spinal fusion is termed the "transition syndrome" which describes the premature degeneration of discs at adjacent levels of the spine. This is certainly the most vexing problem facing relatively young patients when considering spinal fusion surgery.

Many spine experts consider the facet joints to be the most common source of spinal pain. Each vertebra possesses two sets of facet joints, one set for articulating to the vertebra above and one set for the articulation to the vertebra below. In association with the intervertebral discs, the facet joints allow for movement between the vertebrae of the spine. The facet joints are under a constant load from the weight of the body and are involved in guiding general motion and preventing extreme motions in the trunk. Repetitive or excessive trunkal motions, especially in rotation or extension, can irritate and injury facet joints or their encasing fibers. Also, abnormal spinal biomechanics and bad posture can significantly increase stresses and thus accelerate wear and tear on the facet joints.

Recently, technologies have been proposed or developed for disc replacement that may replace, in part, the role of spinal fusion. The principal advantage proposed by complete artificial discs is that vertebral motion segments will retain some degree of motion at the disc space that otherwise would be immobilized in more conventional spinal fusion techniques. Artificial facet joints are also being developed. Many of these technologies are in clinical trials. However, such disc replacement procedures are still highly invasive procedures, which require an anterior surgical approach through the abdomen.

Clinical stability in the spine can be defined as the ability of the spine under physiologic loads to limit patterns of displacement so as to not damage or irritate the spinal cord or nerve roots. In addition, such clinical stability will prevent incapacitating deformities or pain due to later spine structural changes. Any disruption of the components that stabilized a vertebral segment (e.g., disc, facets, ligaments) decreases the clinical stability of the spine.

SUMMARY OF THE INVENTION

Improved devices and methods are needed for treating dysfunctional intervertebral discs and facet joints to provide clinical stability, in particular: (i) implantable devices that can be introduced to offset vertebral loading to treat disc degenerative disease and facets through least invasive procedures; (ii) implants and systems that can restore disc height and foraminal spacing; (iii) implants and systems that can re-distribute loads in spine flexion, extension, lateral bending and torsion, and (iv) implants and systems of the preceding types that are easily removable and/or revisable.

In some embodiments, a bone anchor configured for revision can comprise an elongated body configured for insertion into cancellous bone. The body can comprise a plurality of separate extension elements configured for insertion and withdrawal from the bone. The plurality of separate extension elements may be configured for independent insertion and withdrawal from bone or assembled insertion and independent withdrawal from bone. The body can further include a head in some embodiments.

In certain embodiments, the head can couple the extension elements. In some embodiments the extension elements can be coupled to a core. The extension elements can have many different shapes including, a cross-section that tapers in the distal direction, a smooth exterior surface, an atraumatic tip, a threaded outer surface and/or ridges. In some embodiments, at least one extension element can have an interior passageway for allowing a fluid flow, such as bone cement, therethrough. In some embodiments, the elongated body can be configured to pass into the bone through a single bore in the bone.

In some embodiments, a revisable anchor system for anchoring within a vertebral body, can comprise an elongated body having a proximal end and a distal end, a first extension portion extending at a first angle from the proximal end and a second extension portion extending at a second angle from the proximal end. The proximal body can further include a head configured to maintain the first and second extension portions at the first and second angles.

A method according to certain embodiments of anchoring a treatment apparatus in weakened cancellous bone can comprise (a) providing a bone anchor having a head portion configured with a plurality of separate extension elements configured for independent translation relative to one another; and (b) serially introducing the plurality of separate extension elements into cancellous bone at divergent angles relative to the head portion.

Some methods can further include the step of introducing bone cement into the cancellous bone about the extension elements. This introducing can be accomplished through the head portion and/or by cement flow through at least one extension element.

A further method can be for revisably anchoring spine treatment apparatus. The method can comprise (a) providing a bone anchor comprising an assembly having an anchor body and a plurality of separate extension elements configured for independent translation relative to the anchor body; (b) introducing the plurality of separate extension elements into vertebral cancellous bone; (c) introducing bone cement into the cancellous bone about the extension elements; (d) coupling spine treatment apparatus to the anchor body; (e) de-coupling the spine treatment apparatus from the anchor body after a treatment interval; and (f) revising the bone anchor by serial removal of each separate extension element and optional reinsertion of another anchor body together with re-coupling the spine treatment apparatus.

In some embodiments of the method, step (f) can further comprise applying proximally-directed forces on each extension element to remove the extension elements from the combination of bone cement and cancellous bone, which can include applying axial or helical forces on each extension element.

DETAILED DESCRIPTION OF THE PREFERRED EMBODIMENT

Figure 1:
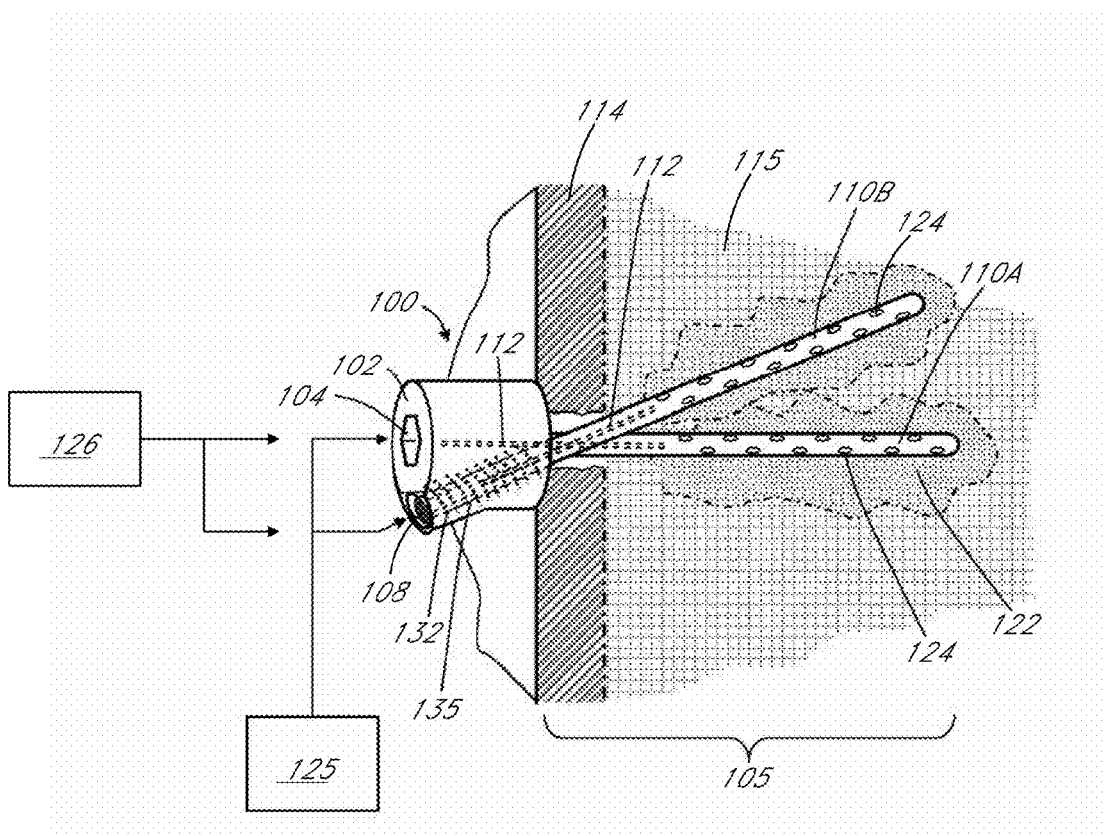
FIG. 1 is a schematic view of a bone anchor system.
Figure 4:
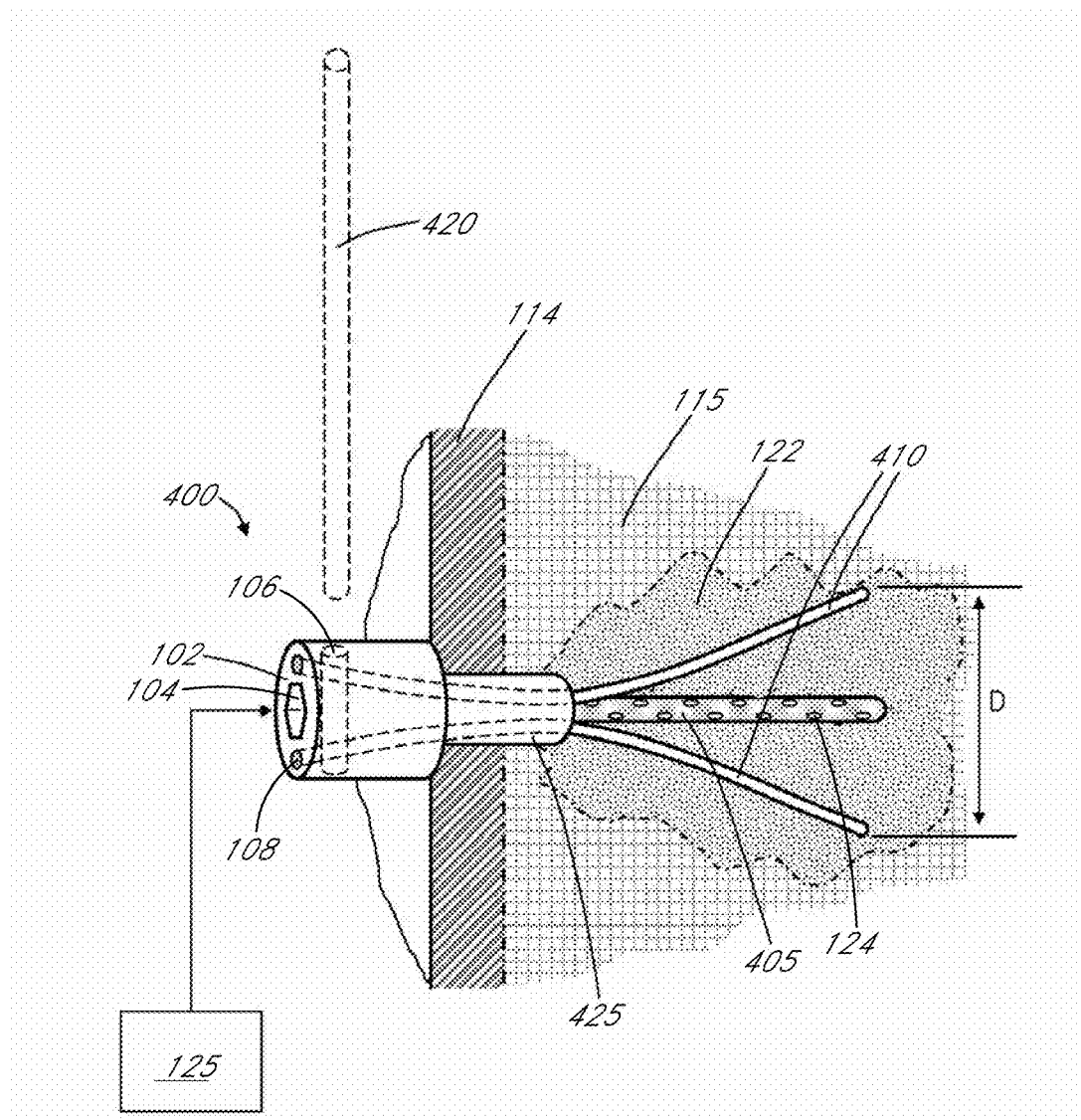
FIG. 4 is a schematic view of another embodiment of a bone anchor system.

Referring to FIG. 1, an apparatus or bone anchor system 100 is shown that is configured for anchoring in bone, such as a vertebral body. Bone anchors as in FIG. 1 can be placed in two or more adjacent vertebrae and thereafter rods or other dynamic stabilization apparatus can be attached to the proximal or head portion 102 of multiple anchor bodies 100 as is known in the art. For example, a rod can be attached to two or more bone anchor systems through a channel or bore 106 in the head portion 102 as shown in FIG. 4. The stabilization apparatus can also be coupled to a screw mechanism (not shown) insertable into a bore 104 in the anchor or another bore 106, 108 or any other connector element in the side of head portion 102. The bores 104, 106, and 108 can be threaded or unthreaded and can include other features to ease insertion of a stabilization apparatus, facilitate assembly and/or prevent detachment after assembly.

The anchor 100 is shown with an extension portion 105 that comprises a plurality of separate extending or extension elements, such as elements 110A and 110B, that extend from or are coupled to the head portion 102 of the anchor. Either or both the extension elements 110A and 110B can be a biocompatible metal, such as a titanium or stainless steel alloy, or a biocompatible polymer in the form of a thin-wall or thick-wall sleeve having interior passageway 112. In FIG. 1, it can be seen that two extension elements are shown for convenience, but the number of extension elements can range from 2 to about 10, and preferably is between two and four. The extension elements can have sharp tips for driving into bone or dull tips as shown in FIG. 1.

The head portion 102 of the anchor 100 of FIG. 1 can have any suitable shape, and can be particularly configured for coupling spine treatment hardware thereto. In the embodiment of FIG. 1, one extension element 110A is fixed to head portion 102 which allows for axial insertion of the extension element 110A into a bone, for example in a transpedicular access through cortical bone 114 into vertebral cancellous bone indicated at 115. The anchor head portion 102 and extension element 110A are configured with interior channel 112 for allowing a flow of bone cement 122 through open terminations or outlets 124 in the extension element. The bone cement can be PMMA and can be delivered by a syringe or cement injector indicated schematically at 125. FIG. 1 shows a plume of cement 122 about the extension elements and interdigitated into cancellous bone 115. The cement injector can be sealably coupled to the extension elements by a rubber gasket, threads or the like.

In a method of use, a bore is made in cortical bone 114 and optionally into cancellous bone 115 after which the extension element 110A is inserted or driven into the bone. Thereafter, cement 122 is injected through the extension element 110A and outwardly of outlets as shown in FIG. 1. After a sufficient volume of cement, for example from about 0.5 cc to 5.0 cc, is injected into the bone, the cement injector is withdrawn. In some methods, a pin or shaft 126 can be inserted into the passageway 112 to force all bone cement outwardly of outlets 124 to allow for easier removal of the extension element in any subsequent revision procedure. The pin or shaft 126 is preferably left in place or can be removed. A next step of some methods comprises introducing a second extension element 110B through a bore 108 in the head portion 102. The second extension element 110B can have a head portion or can be configured without a head portion as depicted in FIG. 1. In one embodiment as in FIG. 1, the proximal end 132 of extension element 110B can have threads 135 for engaging a threaded bore in the head portion 102. As described with respect to the first extension element 110A, the cement injector can then be used to inject bone cement 122 through the second extension element 110B into the cancellous bone 115 to thereby secure the element in the bone. The bore 108 can be threaded or not threaded and can include other features to ease insertion of the extension element 110B, facilitate assembly and/or prevent detachment after assembly.

In some further methods of use, the anchor 100 can be revised as will be described below, which is sometimes necessary in spine treatment procedures as when the anchor loosens or the treatment apparatus requires adjustment. In some embodiments of a revision procedure, the treatment apparatus (e.g., a rod) can be de-coupled from the anchor, the second extension element 110B can then be removed from the bone and head portion 102. This can be done, for example, by engaging the proximal end 132 of the second extension element 110B and rotating it outwardly, which can be facilitated by a smooth exterior surface and an optional distal taper as will be described below. Thereafter, the first extension element 110A can be rotated and removed in a similar manner. Afterwards, a new anchor can be implanted in the bone, and the treatment apparatus can be re-coupled to the revised anchor.

The need for revision can result from screws put in the vertebra in osteoporotic bone. The screw often loosens over time. In some currently available methods, the screw can be revised by replacing it with a larger screw, or an expanding screw. The old anchor would be removed and discarded.

The anchoring systems described above facilitate the easy and simple revision of the anchoring system. Such a revision procedure would not be easy if, for example, a threaded bone screw (e.g., a single threaded screw) were set in bone cement. The anchor systems as described above are well suited for use in osteoporotic vertebrae wherein bone cement is needed to add strength and cancellous bone is too weak for a single threaded bone screw.

According to certain embodiments, a new anchor can be inserted in the same spot (e.g., in vertebrae) as the previous anchor and bone cement can also be injected. The new anchor and bone cement can engage both the bone and the old cement bolus.

The embodiments described herein can prevent loosening. In addition, multiple extension elements can advantageously distribute loads around the cement bolus. As another feature, the anchor can allow for easy removal—in the case where the entire anchor and cement did loosen or the treatment apparatus needs adjustment.

In one aspect of the disclosure, a bone anchor can be provided that comprises: (i) a proximal head configured for coupling to spine treatment apparatus, (ii) a plurality of extension elements configured for insertion through a small bore in cortical bone wherein the extension element are configured to diverge from one another in cancellous bone. In some embodiments, each of the plurality of extension elements can be configured for bone cement injection through an internal passageway. In some embodiments, each of the plurality of extension elements can have a substantially smooth exterior surface for permitting later extraction from hardened bone cement. In some embodiments, each of the plurality of extension elements can have a cross-section that tapers in the distal direction to facilitate later extraction from the hardened cured bone cement.

As can be understood from FIG. 1, the bone cement anchor 100 can provide an excellent anchor since it offers substantial resistance to axial pull-out, rotation and bending. This is because of the large surface area of the extension portion 105 that engages the combination of cancellous bone 115 and interdigitated bone cement 122.

In one aspect, a bone anchor can be provided that comprises an elongated body configured for insertion into a bore in bone, where the body comprises a plurality of separate extension elements that extend at divergent angles in cancellous bone to provide a maximum cross-section or transverse dimension in at least one direction in cancellous bone that is at least 2×, 3× or 4× the dimension of the anchor portion that extends through cortical bone.

In one aspect, a bone anchor can be provided that comprises an elongated body configured for insertion into a bore in bone, and the body can comprise a plurality of separate extension elements configured for independent insertion and withdrawal from bone. The bone anchor can have extension elements that can be coupled to a proximal anchor head portion by threads or by a non-threaded connection. The bone anchor can have at least one extension element with an interior passageway for allowing a fluid flow or bone cement flow therethrough. Such an extension element can have an interior passageway that communicates with a plurality of open terminations 124 in an exterior of the extension element.

An extension element can be fabricated in certain embodiments of a shape memory alloy, or a polymer that can be bioabsorbable or biodegradable. In one embodiment, the extension element has a cross-section that tapers in the distal direction to facilitate withdrawal from bone in a revision procedure. In other embodiments, the extension elements have a smooth surface to facilitate withdrawal from bone cement and bone.

In some embodiments, the extension elements are de-matable from the proximal head portion of the anchor. In other embodiments, at least one extension element is not de-matable from the proximal head portion.

Figure 2:
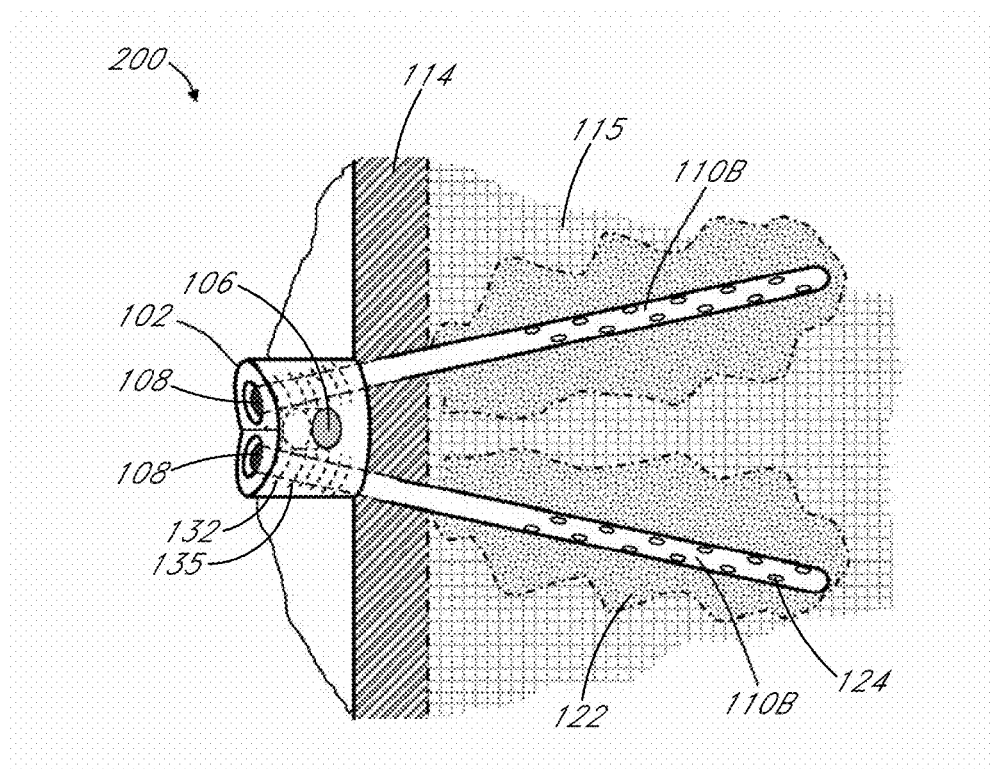
FIG. 2 is a schematic view of another embodiment of a bone anchor system.

Turning now to FIG. 2, an alternative anchor embodiment 200 is illustrated which is similar in some respects to that of FIG. 1. As can be seen, the anchor 200 can include a head 102 having a plurality of bores 108. The bores 108 can be configured to receive extension elements 110B. One way in which the anchor 200 is different from that shown in FIG. 1 is that both of the extension elements 110B are separable from the anchor head portion 102. In addition, the head portion 102 also can include a bore 106 for receiving a dynamic stabilization apparatus as described above. The injection of bone cement 122 can also be utilized as described in the embodiment of FIG. 1.

Figure 3:
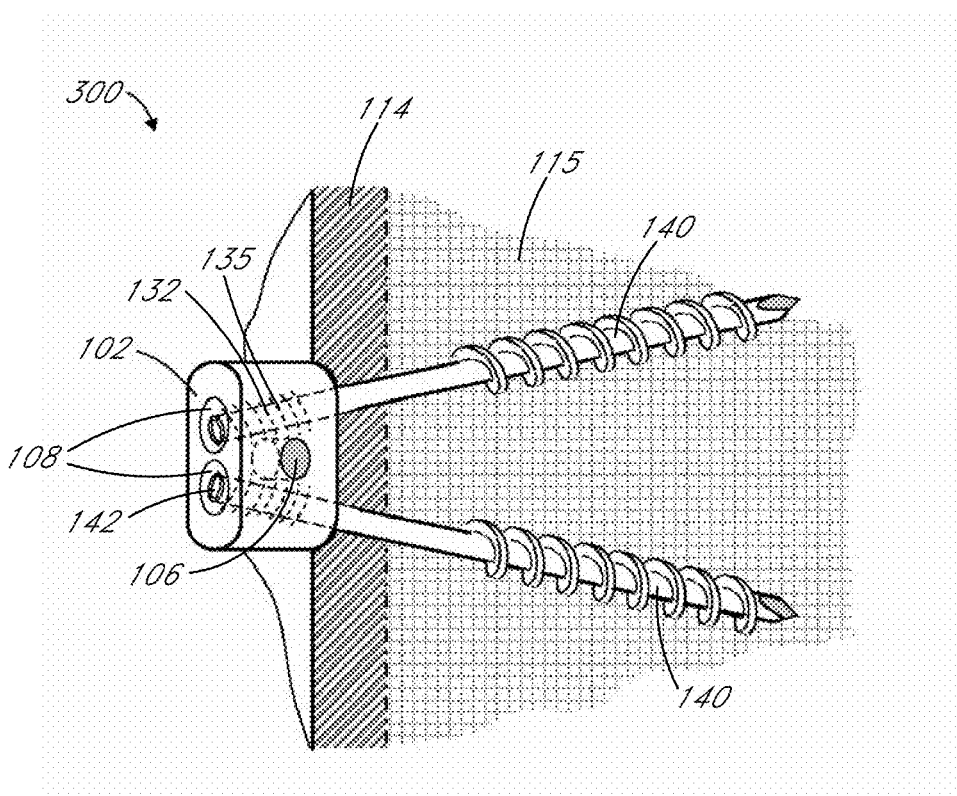
FIG. 3 is a schematic view of another embodiment of a bone anchor system.

FIG. 3 illustrates an alternative anchor embodiment 300 which is similar to that of FIG. 2 except that both the first and second extension elements 140 are configured as bone screws and can be used without bone cement. The screw extension elements 140 can be configured with any type of head portion 142 for engaging with a driving tool (not shown). Such an anchor can be useful in weakened osteoporotic bone where multiple small screws would be preferred over a larger screw. Also, such multiple screws would be generally preferred in pedicles of certain vertebral bodies where two smaller diameter screws would fit within a narrow cross-section pedicle better than one larger diameter screw.

In general, the disclosure provides a revisable anchor system for anchoring within a vertebral body. Some embodiments of an anchor system can comprise an elongated body having a proximal and a distal end, a first extension portion extending at a first angle from the proximal end, and a second extension portion extending at a second angle from the proximal end. The anchor system can be configured to maintain the first and second extension portions at the first and second angles. The anchor system can be configured so that the first and second extension portions are separable and removable independently from one another. In some embodiments, at least one of the extension elements has a threaded exterior surface.

In one method for anchoring a treatment apparatus in weakened cancellous bone, the method can comprise (a) providing a bone anchor having a head portion configured with a plurality of separate extension elements configured for independent translation relative to the head portion, (b) serially introducing the plurality of separate extension elements into cancellous bone at divergent angles relative to the head portion. The method can further include providing an extension element with a threaded portion for engaging cancellous bone. The method can further include providing each extension element with a cross section that tapers in the distal direction for facilitating removal. The method can further include providing an extension element with a smooth surface for facilitating removal. The method can further include introducing bone cement into the cancellous bone about the extension elements. The method can further include introducing the bone cement through the head portion of the anchor. The method can further include introducing the bone cement through at least one extension element.

Some methods for revisably anchoring spine treatment apparatus can comprise (a) providing a bone anchor comprising an assembly of an anchor body and a plurality of separate extension elements configured for independent translation relative to the anchor body, (b) introducing the plurality of separate extension elements into vertebral cancellous bone together with introducing bone cement into the cancellous bone about the extension elements, (c) coupling spine treatment apparatus to the anchor body, (d) de-coupling the spine treatment apparatus from the anchor body after a treatment interval, and (e) removing or revising the bone anchor by serial removal of each separate extension element and optional insertion of a new bone anchor together with re-coupling the spine treatment apparatus. The method can include providing each extension element with a cross section that tapers in the distal direction for facilitating removal. The method can include applying proximally-directed forces (axial and/or helical) on each extension element to remove the extension elements from the combination of bone cement and cancellous bone.

Referring now to FIG. 4, an alternative anchor embodiment 400 which can be utilized in methods described herein is illustrated. The anchor 400 can include a head portion 102, an intermediate portion 425, an extension portion 405, and a plurality of extension elements 410. The head portion 102 can allow injection of bone cement 122 therethrough into extension portion 405. Extension portion 405 can comprise a sleeve, such as a metal sleeve, polymer sleeve or the like that can be removed or left in place in a revision procedure. The extension portion 405 can be integral with the head 102 and intermediate 425 portions, as shown, or may be separable therefrom. The anchor head 102 can allow for a plurality of extension elements 410 to be inserted into the bone. The anchor head 102 can also include a bore 106 to secure a spine treatment apparatus indicated at 420. The plurality of extension elements 410 and the bone cement can allow for secure anchoring of the implant and attached spine treatment apparatus 420 to bone.

In a revision procedure, the elements 410 can be removed one by one. Each element 410 can have a head portion (not shown) for gripping. The elements 410 can be a shape memory alloy and can be keyed with the head portion 102 to insure the curve portion, or other shape feature of the element extends in a desired direction in bone. In some embodiments, the extension elements 410 extend at divergent angles in cancellous bone 115 to provide a maximum cross-section or transverse dimension indicated at D that is at least 2×, 3× or 4× the dimension of the intermediate portion 425 that extends through cortical bone.

Figure 5A:
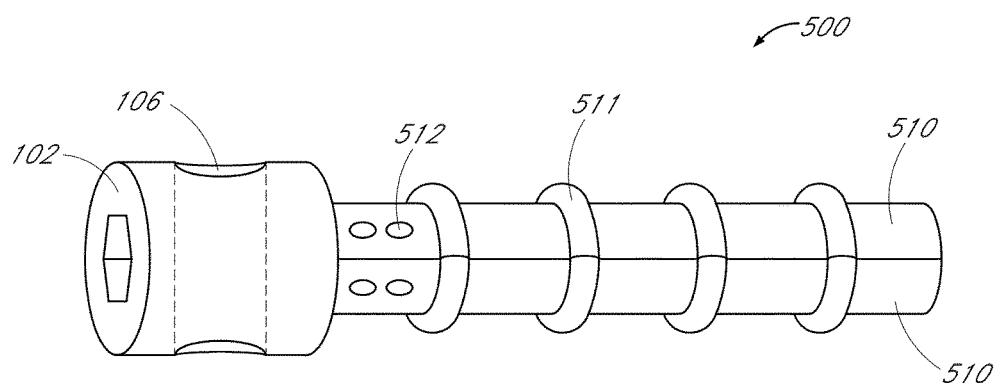
FIGS. 5A-B are schematic views of another embodiment of a bone anchor system in assembled and exploded views respectively.
Figure 5B:
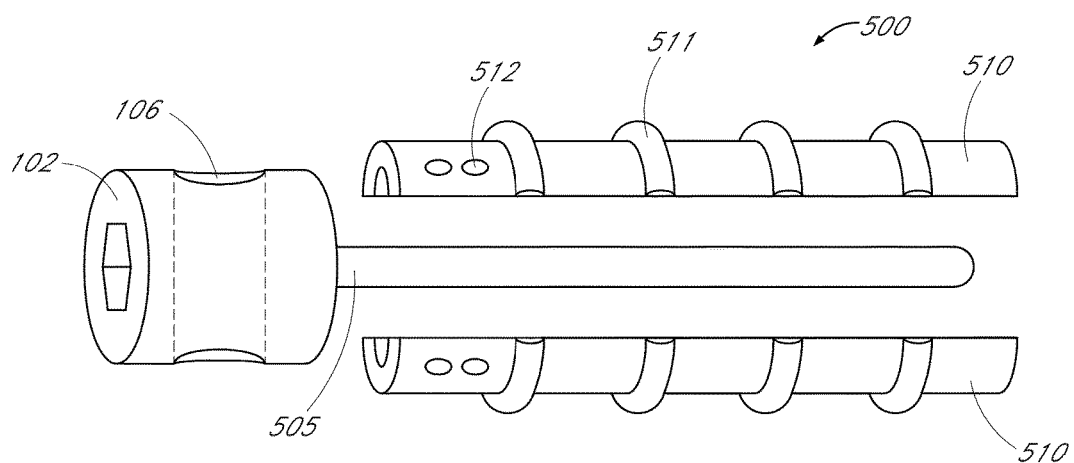

In FIGS. 5A-B, a bone anchor 500 is provided that is configured for revision of treatment. The anchor body can comprise an assembly including a core portion or pin 505 and a plurality of cooperating extension elements 510 that are assembled around the core portion or pin. The plurality of cooperating extension elements 510 can number from about 2 to 6, in some embodiments. The extension elements 510 can include a raised feature indicated at 511 for preventing pullout from a cemented-in condition in bone. The assembled anchor can have a tapered shape in the distal direction to facilitate extraction. Each of the core portion 505 and elements 510 can be configured with a grip mechanism for allowing gripping with a tool to remove the pin or element. In the embodiment of FIGS. 5A-B, the grip mechanism includes at least one bore 512 for engaging with a pulling tool (not shown). In other embodiments, the core 505 can have an interior passageway that communicates with apertures in the extension elements (not shown) to allow for bone cement infusion therethrough similar to that depicted in the embodiments of FIGS. 1 and 2.

In a method of use, it can be understood that the anchor 500 can be set in bone cement and cancellous bone. In a revision procedure, the core 505 can be pulled out initially, and thereafter the extension elements 510 can be pulled out serially through space originally occupied by the assembled anchor. This can be done even with the combination of bone cement and bone remaining intact.

In another embodiment (not shown), an anchor body such as in FIG. 1 can have at least two divergent extension elements with one element being screw threaded for initial engagement with bone and at least one other element being non-threaded with a passageway therein for cement delivery as in FIGS. 1 and 2.

The above description is intended to be illustrative and not exhaustive. Particular characteristics, features, dimensions and the like that are presented in dependent claims can be combined and fall within the scope of the disclosure. The invention also encompasses embodiments as if dependent claims were alternatively written in multiple dependent claim format with reference to other independent claims. Specific characteristics and features and methods are described in relation to some figures and not in others, which is for convenience only. While the principles of the disclosure have been made clear in the exemplary descriptions and combinations, it will be obvious to those skilled in the art that modifications may be utilized in the practice of thereof which are particularly adapted to specific environments and operative requirements without departing from the principles described herein.

Of course, the foregoing description is that of certain features, aspects and advantages, to which various changes and modifications can be made without departing from the spirit and scope of the present invention. Moreover, the bone treatment systems and methods need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A revisable bone anchor system comprising:
an elongated body configured for insertion into a vertebral body comprising outer cortical bone and inner cancellous bone, the elongated body comprising:
a head having a proximal end and a distal end, the head defining a first separate and fixed bore and a second separate and fixed bore, the two separate and fixed bores extending at divergent angles from one another through the head; and
a first extension portion and a second extension portion;
the elongated body comprising a fully implanted configuration wherein the distal end of the head is configured to abut against an exterior of the cortical bone, the first extension portion extends through the first separate and fixed bore beyond the distal end of the head at a first angle with respect to the head and the second extension portion extends through the second separate and fixed bore beyond the distal end of the head at a second angle with respect to the head, wherein the first and second extension portions are configured for insertion through the cortical bone and into the cancellous bone, and wherein the first and second extensions portions are non-parallel, so as to provide substantial resistance to axial pull-out of the elongated body when fully implanted in bone,
wherein at least one of the extension portions has an interior passageway for allowing a fluid flow therethrough, and
wherein the head comprises a hole extending in a first direction, the hole configured to lockingly engage with a rod for stabilizing a spine segment portion, wherein proximal ends of the extension portions reside proximal to the hole in the fully implanted configuration,
wherein the head comprises a height in a second direction, the second direction transverse to the first direction, and wherein the head comprises a width in a third direction, the third direction transverse to the first direction and transverse to the second direction,
wherein the head has a height less than the first and second extension portions in the second direction and a width less than the first and second extension portions the third direction.

2. The anchor system of claim 1, wherein the head is configured to maintain the first and second extension portions at the first and second angles.

3. The anchor system of claim 2, wherein the head is separable from the first and second extension portions.

4. The anchor system of claim 1, wherein the first and second extension portions are separable.

5. The anchor system of claim 1, wherein at least one of the extension portions has a threaded outer surface.

6. The anchor system of claim 1, wherein at least one of the extension portions is non-threaded.

7. The anchor system of claim 6, wherein each of the extension portions has an interior passageway for allowing a fluid flow therethrough.

8. The anchor system of claim 1, wherein the interior passageway communicates with a plurality of open terminations in an exterior of the extension portion having the interior passageway.

9. The anchor system of claim 1, wherein the elongated body has a proximal transverse dimension and a distal transverse dimension that is at least twice the dimension of the proximal transverse dimension, wherein the distal transverse dimension is provided by distal ends of the first and second extension portions.

10. The anchor system of claim 1, wherein the first and second extension portions are configured for separate insertion and withdrawal from the elongated body to permit a revision procedure.

11. The anchor system of claim 1, wherein at least one of the first and second extension portions is configured to be inserted through one of the bores in the head.

12. The anchor system of claim 1, wherein proximal ends of the first and second extension portions are laterally adjacent to one another.

13. The anchor system of claim 1, wherein the bores in the head are threaded, wherein the first extension portion and the second extension portion include threads on a proximal end thereof configured to engage with one of the bores in the head.

14. The anchor system of claim 1, wherein the first and second extensions portions extend at divergent angles from one another relative to the head, wherein the first and second angles are defined by the bores in the head.

* * * * *

UNITED STATES PATENT AND TRADEMARK OFFICE
CERTIFICATE OF CORRECTION

PATENT NO. : 9,597,118 B2
APPLICATION NO. : 12/683358
DATED : March 21, 2017
INVENTOR(S) : Csaba Truckai et al.

Page 1 of 1

It is certified that error appears in the above-identified patent and that said Letters Patent is hereby corrected as shown below:

In the Claims

Column 9, Line 26 reads, "... first and second extensions portions ..." which should read, "... first and second extension portions ..."

Column 9, Line 45 reads, "... second extension portions the third ..." which should read, "... second extension portions in the third ..."

Column 10, Line 43 reads, "... second extensions portions extend ..." which should read, "... second extension portions extend ..."

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*